(12) United States Patent
Stinnette

(10) Patent No.: US 7,909,882 B2
(45) Date of Patent: Mar. 22, 2011

(54) SOCKET AND PROSTHESIS FOR JOINT REPLACEMENT

(76) Inventor: Albert Stinnette, Zephyrhills, FL (US)

(*) Notice: Subject to any disclaimer, the term of this patent is extended or adjusted under 35 U.S.C. 154(b) by 982 days.

(21) Appl. No.: 11/625,277

(22) Filed: Jan. 19, 2007

(65) Prior Publication Data
US 2008/0177395 A1 Jul. 24, 2008

(51) Int. Cl.
*A61F 2/32* (2006.01)
(52) U.S. Cl. .......... 623/23.41; 623/23.4; 623/22.15
(58) Field of Classification Search ...... 623/13.11–13.2, 623/18.11, 19.12, 20.22, 21.15–21.17, 23.4, 623/23.41, 23.39, 23.12–23.14, 22.15
See application file for complete search history.

(56) References Cited

U.S. PATENT DOCUMENTS

| | | | |
|---|---|---|---|
| 2,765,787 A * | 10/1956 | Pellet | 623/23.27 |
| 4,441,496 A | 4/1984 | Shalaby et al. | |
| 4,544,516 A | 10/1985 | Hughes et al. | |
| 4,576,608 A | 3/1986 | Homsy | |
| 4,776,851 A * | 10/1988 | Bruchman et al. | 623/13.11 |
| 4,808,186 A | 2/1989 | Smith | |
| 4,822,368 A | 4/1989 | Collier | |
| 5,004,474 A * | 4/1991 | Fronk et al. | 623/13.14 |
| 5,010,145 A | 4/1991 | Ikada et al. | |
| 5,116,372 A | 5/1992 | Laboureau | |
| 5,163,961 A * | 11/1992 | Harwin | 623/22.46 |
| 5,250,049 A | 10/1993 | Michael | |
| 5,443,516 A | 8/1995 | Albrektsson et al. | |
| 5,534,033 A * | 7/1996 | Simpson | 623/13.14 |
| 5,540,697 A | 7/1996 | Rehmann et al. | |
| 5,549,701 A | 8/1996 | Mikhail | |
| 5,683,471 A | 11/1997 | Incavo et al. | |
| 5,702,474 A * | 12/1997 | McCandliss | 623/13.12 |
| 5,725,590 A | 3/1998 | Maumy et al. | |
| 5,728,099 A | 3/1998 | Tellman | |
| 5,741,256 A | 4/1998 | Bresina | |
| 5,755,807 A | 5/1998 | Anstaett et al. | |

(Continued)

FOREIGN PATENT DOCUMENTS

EP 0288041 B1 9/1996

(Continued)

OTHER PUBLICATIONS

Printout of http:///www.ortho.smith-nephew.com/us/Standard.asp?NodeID=3713, Birmingham Hip Resurfacing System, Smith & Nephew, pp. 1 & 2.

(Continued)

*Primary Examiner* — Corrine M McDermott
*Assistant Examiner* — Megan Wolf
(74) *Attorney, Agent, or Firm* — Christopher Paradies; Fowler White Boggs P.A.

(57) ABSTRACT

A joint replacement prosthesis and procedure reduce the number of steps to complete a joint replacement. The joint replacement prosthesis comprises a ball and socket unit that fixes the ball in the socket prior to surgery. The unit is coupled to a bone structure in the patient and is coupled with a prosthesis that is fixed to another bone of the patient, such as a femoral implant fixed in a femur and providing a coupling at the end of a neck portion that is easily fit into a femoral head and acetabulum unit. A tether may be used to retain the ball in the socket and/or the ball may be retained by extension in the socket that do not restrict patient motion.

5 Claims, 16 Drawing Sheets

U.S. PATENT DOCUMENTS

| | | | |
|---|---|---|---|
| 5,759,184 A | 6/1998 | Santangelo | |
| 5,766,174 A | 6/1998 | Perry | |
| 5,766,180 A | 6/1998 | Winquist | |
| 5,779,705 A | 7/1998 | Matthews | |
| 5,800,557 A * | 9/1998 | Elhami | 623/23.12 |
| 5,853,387 A | 12/1998 | Clegg et al. | |
| 5,855,579 A | 1/1999 | James et al. | |
| 5,871,492 A | 2/1999 | Sorensen | |
| 5,908,422 A | 6/1999 | Bresina | |
| 5,928,231 A | 7/1999 | Klein | |
| 5,951,605 A * | 9/1999 | Dennis et al. | 623/13.11 |
| 5,973,223 A | 10/1999 | Tellman et al. | |
| 6,004,324 A | 12/1999 | Gahr et al. | |
| 6,033,407 A | 3/2000 | Behrens | |
| 6,034,295 A | 3/2000 | Rehberg et al. | |
| 6,074,392 A | 6/2000 | Durham | |
| 6,077,264 A | 6/2000 | Chemello | |
| 6,077,265 A | 6/2000 | Werding et al. | |
| 6,123,708 A | 9/2000 | Kilpela et al. | |
| 6,143,012 A | 11/2000 | Gausepohl | |
| 6,187,006 B1 | 2/2001 | Keller | |
| 6,187,007 B1 | 2/2001 | Frigg et al. | |
| 6,221,074 B1 | 4/2001 | Cole et al. | |
| 6,228,086 B1 | 5/2001 | Wahl et al. | |
| 6,228,122 B1 * | 5/2001 | McGann | 623/23.11 |
| 6,238,126 B1 | 5/2001 | Dall | |
| 6,261,290 B1 | 7/2001 | Friedl | |
| 6,270,499 B1 | 8/2001 | Leu et al. | |
| 6,277,397 B1 | 8/2001 | Shimizu | |
| 6,319,255 B1 | 11/2001 | Grundei et al. | |
| 6,328,764 B1 | 12/2001 | Mady | |
| 6,348,053 B1 | 2/2002 | Cachia | |
| 6,379,360 B1 | 4/2002 | Ackeret et al. | |
| 6,383,185 B1 | 5/2002 | Baumgart | |
| 6,383,223 B1 * | 5/2002 | Baehler et al. | 623/21.11 |
| 6,387,098 B1 | 5/2002 | Cole et al. | |
| 6,402,787 B1 | 6/2002 | Pope et al. | |
| 6,406,477 B1 | 6/2002 | Fujiwara | |
| 6,409,730 B1 | 6/2002 | Green et al. | |
| 6,423,066 B1 | 7/2002 | Harder et al. | |
| 6,448,890 B1 | 9/2002 | Cooper | |
| 6,451,058 B2 | 9/2002 | Tuke et al. | |
| 6,461,360 B1 | 10/2002 | Adam | |
| 6,488,684 B2 | 12/2002 | Bramlet et al. | |
| 6,488,715 B1 | 12/2002 | Pope et al. | |
| 6,491,714 B1 | 12/2002 | Bennett | |
| 6,511,481 B2 | 1/2003 | von Hoffmann et al. | |
| 6,517,583 B1 | 2/2003 | Pope et al. | |
| 6,547,791 B1 | 4/2003 | Buehren et al. | |
| 6,558,388 B1 | 5/2003 | Bartsch et al. | |
| 6,569,165 B2 | 5/2003 | Wahl et al. | |
| 6,575,974 B2 | 6/2003 | Gotfried | |
| 6,575,976 B2 | 6/2003 | Grafton | |
| 6,579,294 B2 | 6/2003 | Robioneck | |
| 6,602,293 B1 | 8/2003 | Biermann et al. | |
| 6,632,224 B2 | 10/2003 | Cachia et al. | |
| 6,652,529 B2 | 11/2003 | Swanson | |
| RE38,409 E | 1/2004 | Noiles | |
| 6,702,823 B2 | 3/2004 | Iaia | |
| 6,887,243 B2 | 5/2005 | Culbert | |
| 6,890,333 B2 | 5/2005 | von Hoffmann et al. | |
| 6,908,465 B2 | 6/2005 | von Hoffmann et al. | |
| 6,921,400 B2 | 7/2005 | Sohngen | |
| 6,926,719 B2 | 8/2005 | Sohngen et al. | |
| 7,008,425 B2 | 3/2006 | Phillips | |
| 7,022,348 B2 | 4/2006 | Ketharanathan | |
| 7,070,601 B2 | 7/2006 | Culbert et al. | |
| 7,077,867 B1 | 7/2006 | Pope et al. | |
| 2002/0120270 A1 | 8/2002 | Trieu et al. | |
| 2002/0177854 A1 | 11/2002 | Tuke et al. | |
| 2002/0197296 A1 | 12/2002 | Gen | |
| 2003/0187512 A1 | 10/2003 | Frederick et al. | |
| 2003/0191537 A1 | 10/2003 | Wasielewski | |
| 2003/0229357 A1 | 12/2003 | Dye | |
| 2004/0097943 A1 * | 5/2004 | Hart | 606/72 |
| 2004/0267360 A1 | 12/2004 | Huber | |
| 2005/0042252 A1 | 2/2005 | Tanaka et al. | |
| 2005/0053671 A1 | 3/2005 | Tanaka et al. | |
| 2005/0171614 A1 * | 8/2005 | Bacon | 623/22.19 |
| 2006/0210601 A1 | 9/2006 | Yunoki et al. | |
| 2007/0004035 A1 | 1/2007 | Sitzmann | |
| 2007/0255420 A1 | 11/2007 | Johnson et al. | |
| 2009/0076619 A1 | 3/2009 | Grappiolo et al. | |

FOREIGN PATENT DOCUMENTS

| | | |
|---|---|---|
| EP | 0943346 A1 | 9/1999 |
| EP | 1230938 A1 | 8/2002 |
| EP | 1442756 A2 | 8/2004 |
| EP | 1270660 B1 | 12/2004 |
| EP | 1053031 B1 | 10/2005 |
| EP | 1021990 B1 | 12/2005 |
| EP | 1611852 A2 | 1/2006 |
| WO | 9722301 A1 | 6/1997 |

OTHER PUBLICATIONS

Printout of http://www.zimmer.com/z/ctl/op/global/action/1/id/9223/template/MP/prcat/M2/prod/y, Zimmer Periarticular Plating System, Zimmer, pp. 1-3.

Printout of http://www.zimmer.com/z/ctl/op/global/action/1/id/8010/template/MP/prcat/M2/prod/y, Epsilon Durasul Constrained Insert, Zimmer, pp. 1-3.

Zimmer Periarticular Distal Lateral Femoral Locking Plate, Zimmer, printout of http://www.zimmer.com/web/enUS/pdf/product_brochures/234710500_pd_lateral_femoral_lp_ds.pdf, 2 pages.

Printout of http://www.zimmer.com/z/ctl/op/global/action/1/id/9215/template/MP/prcat/M2/prod/y, Zimmer ITST Intertrochantric/Subtrochantric Intramed Nail System, Zimmer, pp. 1 & 2.

Printout of http://www.arthrosurface.com/index.php/content/view/112/76, HemiCAP Resurfacing System, Arthrosurface, pp. 1-4.

Duraloc Constrained Liner, DePuy a Johnson & Johnson company, 4 pages.

Pinnacle A Cetabular Cup System, DePuy a Johnson & Johnson company, pp. 1-44.

Ultamet Metal-on-Metal Articulation, Depuy a Johnson & Johnson company, pp. 1-22.

Hans J. Refiar, MD, Preserving the femoral neck in hip replacement: a concept for the future?, Orthopedics Today, p. 4.

Jason Werle, MD, FRCSC et al, The Polyethylene Liner Dissociation in Harris-Galante Acetabular Components, The Journal of Arthroplasty vol. 17. No. 1 2002, pp. 78-81.

Stryker(r) Receives FDA Clearance for LFIT(TM) Anatomic Femoral Heads with X3(R) Liners, Print out of http://biz.yahoo.com/prnews/060825/def010.html?.v=57, 2 pages.

S.J. Caplan, Smith & Nephew Gets a Leg Up, print out of http://biz.yahoo.com/fool/060511/114737837741.html/.v=1, pp. 1 & 2.

Ed Edelson, Experts Predict Hip-Fracture Epidemic, print out of http://news.yahoo.com/s/hsn/20060616/hl_hsn/expertspredicthipfractureepidemic, p. 1 & 2.

Print out of http://www.ortho.smith-nephew.com/us/node.asp?NodeId=3724, Anthology Primary Hip System, Smith & Nephew, 2 pages.

Print out of http://www.ortho.smith-nephew.com/us/node.asp?NodeId=2920, Cobalt Chrome, Smith & Nephew, 1 page.

Print out of http://www.ortho.smith-nephew.com/us/node.asp?NodeId=3761, Oxinium Femoral Heads, Smith & Nephew, 1 page.

Print out of http://www.ortho.smith-nephew.com/us/node.asp?NodeId=2916, Contour Acetabular Rings, Smith & Nephew, 1 page.

Print out of http://www.ortho.smith-nephew.com/us/node.asp?NodeId=2913, Reflection All-Poly, Smith & Nephew, 1 page.

Print out of http://www.ortho.smith-nephew.com/us/node.asp?NodeId=2829, Echelon Revision Hip System, Smith & Nephew, 2 pages.

Print out of http://www.ortho.smith-nephew.com/us/node.asp?NodeId=3727, Emperion Modular Hip System, Smith & Nephew, 2 pages.

Print out of http://www.ortho.smith-nephew.com/us/Standard.asp?NodeId=3708, CPCS Cemented Hip System, Smith & Nephew, 1 page.

Print out of http://www.ortho.smith-nephew.com/us/Standard.asp?NodeId=2897, Echelon HipSystem, Smith & Nephew, 2 pages.
Print out of http://www.ortho.smith-nephew.com/us/Standard.asp?NodeId=3739, Image Porous Hip System, Smith & Nephew, 1 pages.
Print out of http://www.ortho.smith-nephew.com/us/Standard.asp?NodeId=3812, Platform Hip System, Smith & Nephew, 2 pages.
Print out of http://www.orthe.smith-nephew.com/us/Standard.asp?NodeId=2867, Spectron Hip System, Smith & Nephew, 2 pages.
Print out of http://www.ortho.smith-nephew.com/us/Standard.asp?NodeId=2868, Synergy Hip System, Smith & Nephew, 2 pages.
Print out of http://www.ortho.smith-nephew.com/us/Standard.asp?NodeId=3728, Accord Cable System, Smith & Nephew, 1 page.
Print out of http://www.ortho.smith-nephew.com/us/Standard.asp?NodeId=3201, Echelon Revision Cemented, Smith & Nephew, 1 page.
Print out of http://www.ortho.smith-nephew.com/us/Standard.asp?NodeId=3096, Spectron Hip System, Smith & Nephew, 1 page.
Print out of http://www.ortho.smith-nephew.com/us/Standard.asp?NodeId=2911, Impaction Grafting, Smith & Nephew, 1 page.
Print out of http://www.ortho.smith-nephew.com/us/Standard.asp?NodeId=3027, Acetabular Options, Smith & Nephew, 1 page.
Print out of http://www.arthrosurface.com/learnHemiCap.html, HemiCAP Resurfacing System, pp. 1-4.
Printout of http://www.orthosmith-nephew.com/us/Standard.asp?NodelD=3006, Trigen Tan Nail, Smith & Nephew, 2 pages.
Printout of http://www.jnjgateway.com/home.jhtml?loc-USENG&page=viewcontent&contendld=0900..., Milagro Interference Screw, Johnson & Johnson, 2 pages.
Printout of http://www.encoremed.com/products/spine/index.htm, Vari Grip fixation product, Encore Medical Corporation, 2 pages.
Printout of http://www.encoremed.com/products/cyclone/index.htm, Cyclone anterior cervical plate, Encore Medical Corporation, 2 pages.
Trochanteric Reattachment Device, Technique Guide by Synthes, 10 pages.
Gamma3, The Compact Version of the Gamma Nail System, Operative Techniquie, Hip Fracture System, Trochanteric and Long Nails, 1 page.
Stryker, Gamma3(trademark), The Compact Version of the Gamma(trademark) Nail System Operative Technique, Copyright 2004 Stryker, pp. 1-3 and 5-42.
University Orthopaedics, PC, Total Joints, Total Hip Replacement, Copyright 2006 Understand.com, 1 page.

* cited by examiner

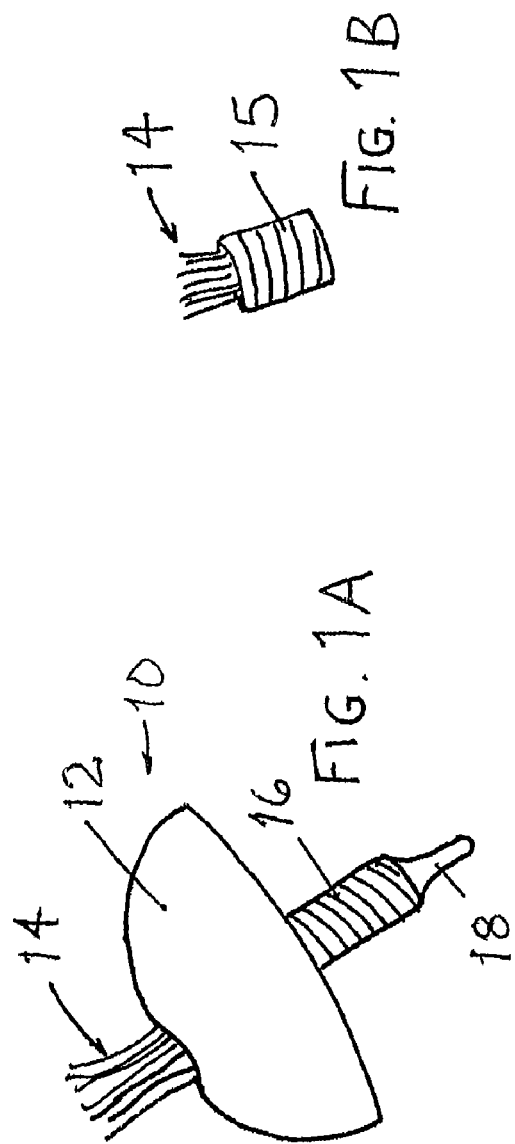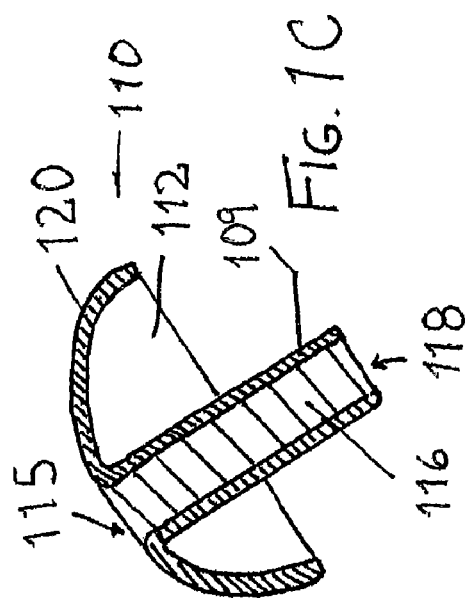

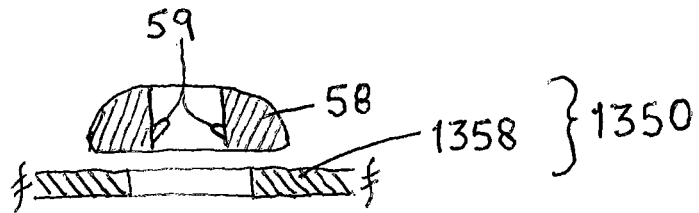
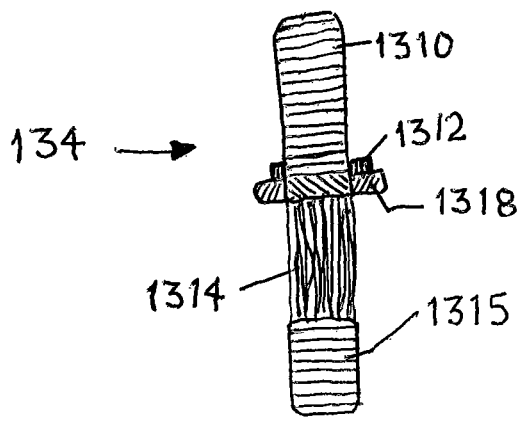
FIG. 13B
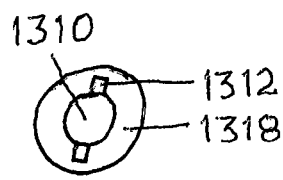
FIG. 13C
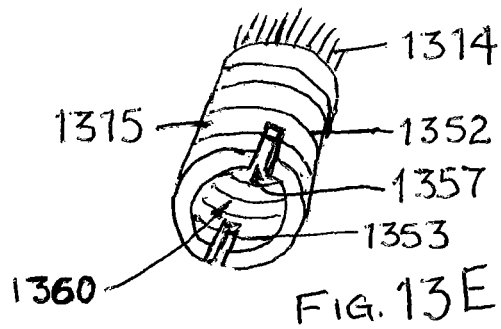
FIG. 13E
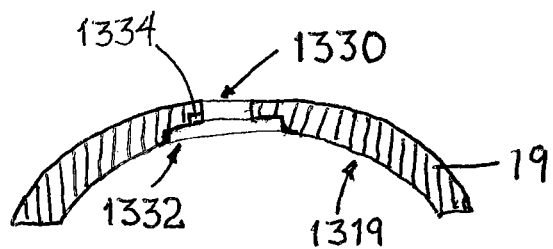
FIG. 13D
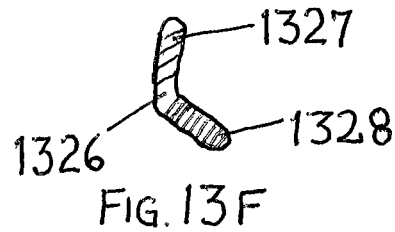
FIG. 13F

SOCKET AND PROSTHESIS FOR JOINT REPLACEMENT

FIELD OF THE INVENTION

The field relates to orthopedics and repair of fractures and wear to load bearing bones and joints.

BACKGROUND

Ball joints and load bearing structures are often damaged by disease, wear and fractures that require repair or replacement of these structures. Several retention mechanisms have been developed that helped to secure load bearing structures and ball and socket joints; however, none of them meet the needs of an aging and increasingly overweight population. Many mechanisms for repair and replacement require unnecessary additional steps during surgery in order to secure and/or retain a prosthesis or to repair a fracture in a bone. FIG. 12 shows a prior art fixation device 54 comprising a capped end 52, a pointed end 56 and a ratchet connector 58 having spades 59 that mate with ridges 40 to adjust the length l between the capped end 52 and the connector 58 using a quick ratchet mechanism locks the spades 59 into the grooves 50 between the ridges 40. There is a long standing unresolved need for efficient and effective methods and devices for use in emergency and elective surgeries to repair and replace damaged bones and joints.

A large fraction of joint replacement surgeries fail due to dislocation of the ball from the socket. Various fixation devices have been designed to retain a ball in the shell of a socket joint, but each of these devices further restricts the range of motion of the ball in the joint. The restricted motion is caused by impingement of one part of a prosthesis against the fixation device or a portion of the shell. Furthermore, any impingement acts as a fulcrum and is capable of causing a large force, through a lever and fulcrum action, that actually causes an increased chance of dislocation. Even worse, the forces can be sufficient to loosen the fixation devices holding the socket in the bone of the patient. Thus, fixation devices that restrict motion are counterproductive and cause dislocations to become even more likely.

SUMMARY

A system of orthopedic repair and joint replacement reduces the number of steps required for completing a procedure and reduces the incidence of dislocations. For example, a socket and prosthesis for joint replacement surgery has a preassembled socket and ball and a prosthesis for insertion into the ball that is retained by a retaining mechanism. The retaining mechanism holding the end of the prosthesis in the ball does not cause any increase in impingement or dislocation. The ball is retained in a shell as a unit by a flexible ligament structure that allows the ball size, shape and movement to mimic that of the joint being replaced without introducing a retaining mechanism that causes an increased incidence of impingement and dislocation.

A surgical method includes insertion of a socket and ball (e.g., a cup and a femoral head) as a unit into a bony structure of the body (e.g. an acetabulum). By inserting a surgically sterilized shell and ball unit in a single step, the method reduces the number of steps to replace the joint, reduces the chances of infection, and eliminates the possibility that debris will be left in the socket prior to insertion of the ball, which debris can cause severe, premature wear in the joint.

In one example, the ball has a cavity and the cavity has a retention mechanism within the cavity for retaining a neck portion of a joint prosthesis fixed in the bone, such as a femoral implant having a neck for coupling a femoral head to the femur of a patient undergoing joint replacement. In another example, the same procedure may be used for repairing other joints, such as knees, fingers, shoulders, ankles, and the like. A prosthesis for coupling with a bone of a patient has a free end shaped to be inserted into the ball and socket joint prosthesis. The free end of the prosthesis fits into the cavity in the ball and is latched by a retention mechanism. The ball and socket unit may be coupled with another bone of the patient using any mechanism for fixation, such as one or more pins, one or more screws, a snap fit, a press fit or any other fixation method compatible with the loads and shear forces applicable for the specific joint replaced.

One advantage of the socket and prosthesis for joint replacement is that the retention mechanism does not require additional steps in the surgical procedure. Another advantage is that no fasteners may be necessary to secure the retention mechanism. Yet another advantage is that the socket and ball unit is inserted as a unit, avoiding the introduction of detritus such as bone chips between the shell and the ball. Yet another advantage is that the ball and socket may be designed more like a natural ball and socket joint, which retains the ball within the socket without unduly restricting movement. Yet another advantage is that the socket may be inserted in a retention system that transfers load to the surrounding bone, preventing bone loss caused by rigid fixtures that distribute loads less naturally to the surrounding bone.

BRIEF DESCRIPTION OF THE FIGURES

The drawings show examples of the present invention, which is not limited to the specific examples as represented in the drawings.

FIGS. 1A-1E illustrate examples for use in describing a ball of a ball and socket unit.

FIGS. 13B-F depict many of the components used in the example of a prosthesis for repairing or replacing a joint.

DETAILED DESCRIPTION

Figure 1D:
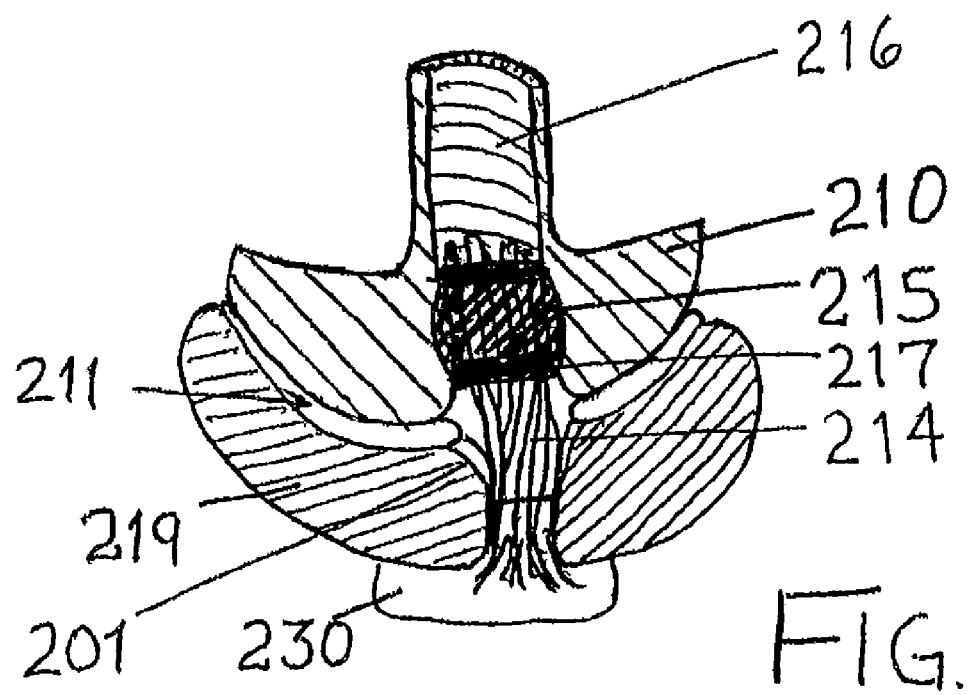
Figure 1E:
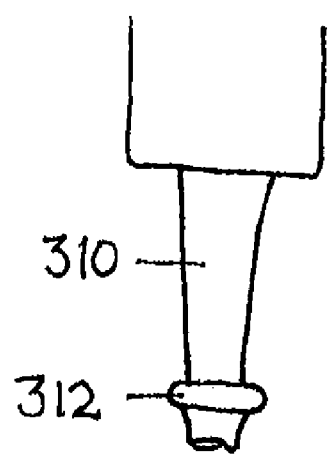

The examples described and drawings rendered are illustrative and are not to be read as limiting the scope of the invention as it is defined by the appended claims. Many variations in the system, changes in specific components of the system and uses of the system will be readily apparent to those familiar with the area based on the drawings and description provided.

In one example, the attachment of the shell, itself, is made by a conventional process, which fixes the shell using lag screws to the bone of a patient. The shell may be located anatomically on a supporting structure or may be reversed and located on a long bone of the patient, such as done in some shoulder replacement procedures. In either alternative, a ball and shell unit is inserted, and the shell holding the ball is fixed to the underlying bone, while the ball is capable of articulated motion within the shell and is attached to a free end of a prosthesis fixed to another bone of the patient.

The example of FIG. 1A shows a solid femoral head replacement for use in a ball and socket unit. A ligament 14 is made of a flexible material, such as fibers, tubes or nanotubes of a biocompatible material, such as carbon (e.g. graphite tubes), boron nitride, silicon-based compounds, a nylon, a polypropylene, or a polyethylene. The ligament may be a natural material or a synthetic material. The ligament 14 couples a shell (not shown in FIG. 1A) to the load bearing surface 12 of the ball 10. The ball 10 in FIG. 1A is a solid material, such as a high density polyethylene, which may be crosslinked, or a metal (e.g. titanium, stainless steel, or other wear resistant metal). An attachment mechanism 16 is coupled or joined to the ball 10, which may have an extension 18, which assists a physician in located and inserting the attachment mechanism 16 in a fixation device (not shown in FIG. 1A).

FIG. 1B shows one example of a coupling device for the ligament 14 in the ball 10. The surface of the attachment mechanism 16 is shown as threaded, but any mechanism may be used for coupling the attachment mechanism 16 in the ball 10. For example, the attachment mechanism may be a formable polymer that is pored in place, when the flexible material of the ligament 14 is inserted in the ball. In one process, a threaded plug 15 is formed that binds flexible strands 14 in a threaded shaft 115 of a femoral head 10, 110, such as shown in FIGS. 1A-1C. In FIG. 1D, another example is shown. A process forms a plug 215, using a resin to form the plug in place, as shown in the example of FIG. 1D, which couples the ligament 214 to the ball 210. The plug 215 fills a void in the ball 210, which has a mechanism that retains the plug 215 in the void. The mechanism shown in FIG. 1D is a larger diameter than the diameter of the shaft on either side of the plug 215. One or more protrusions into the void may be used to lock the plug 215 in place in a void or portion of a shaft formed in the ball 210. For example, an initial plug 217 may be formed on a portion of the ligament 214, which provides a temporary seal to the shaft 216. Then, a resin may be injected into the void in the shaft 216, which when cured binds the ligament 214 in a plug 215. For example, a nipple 310 with a sealing ring 312 may be inserted in the shaft 216 of the ball 210. The sealing ring 312 prevents back flow of resin up the shaft 216, while the void is filled with resin, for example.

Figure 2:
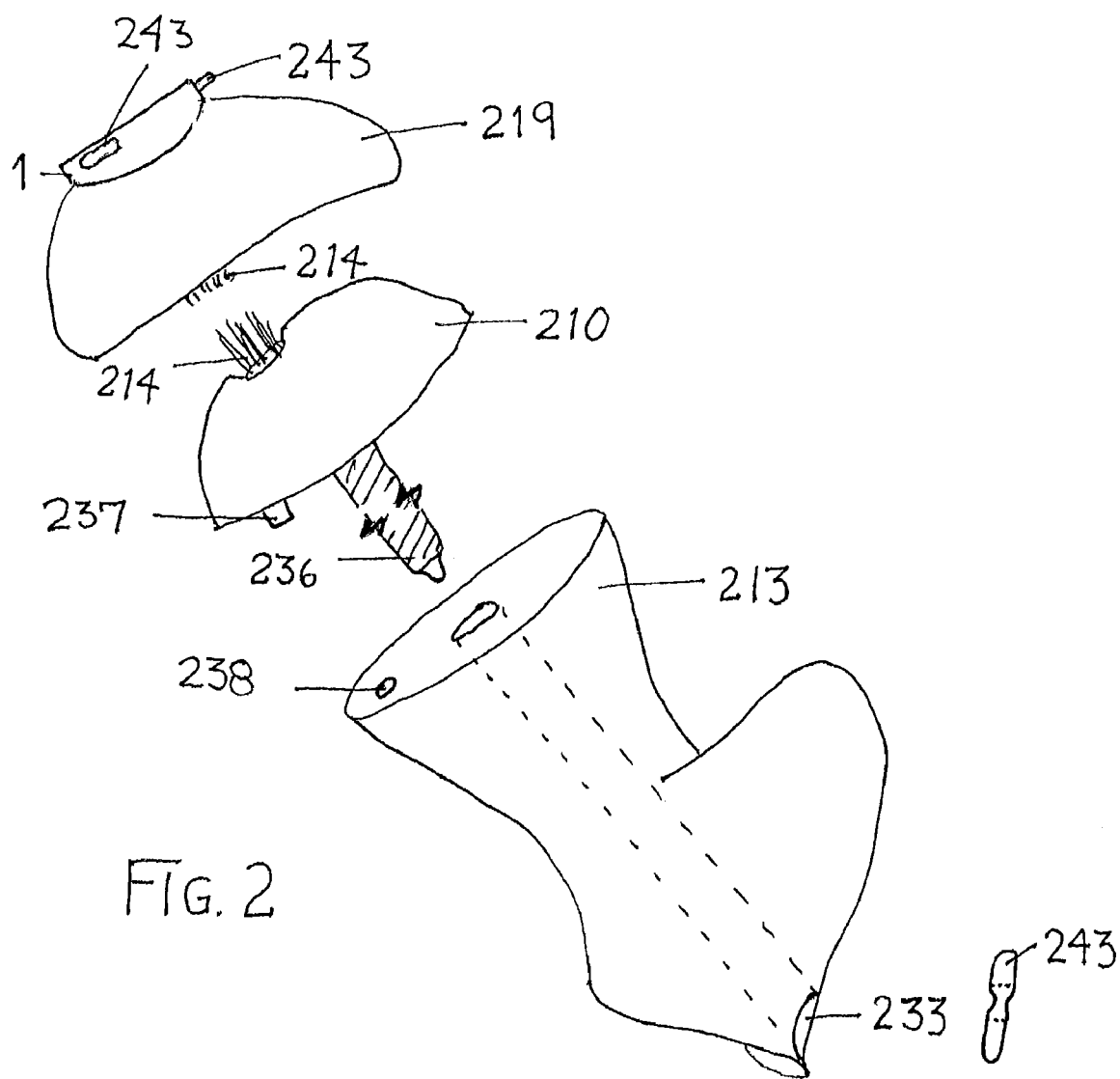
FIG. 2 illustrates an exploded view of an example of a ball and socket implanted on the end of a femur.

FIG. 2 illustrates, schematically in an exploded view, another example of ball and socket replacement for use in hip replacement surgery. The ball 210 and the shell 219 are coupled by a ligament 214. The femoral head is removed from the femur or is shaved as is known in the art from the femur 213. A hole 233 is drilled through a portion of the femur 213. An attachment mechanism 236 extends from the replacement femoral head 210 through the hole 233, and the attachment mechanism 236 may be coupled to the femur 213 using a retainer 243, which may be threaded, snap fit, friction welded, heat welded, latched, pinned, or otherwise fastened in place. Any portion of the attachment mechanism 236 extending from the hole 233 may be removed flush with the retainer 243. The retainer 243 may be of any size and shape and may be shaped to the femur 213 or other bone. In one example, the retainer 243 extends down the outside of the femur 213 and uses additional fasteners to hold the retainer 243 in place and support more loads. This may be preferred if the femur 213 has been compromised by fractures or bone loss, for example. In one example, the retainer 243 has ridges that interlock with ridges on the shaft of the attachment mechanism 236. The retainer 243 is fit over the attachment mechanism 236 and a mechanical gun is used to draw the retainer 243 up the shaft of the attachment mechanism 236 until a preset tension is applied on the attachment mechanism 236. The preset tension may be used to draw the replacement head 210 into intimate contact with the femur 213. An optional pin or projection 237 may dig into the bony structure of the femur 213 or may mate with a prepared hole 238 to prevent rotation of the head 210. The shell 219 may be snap fit or otherwise fit into a mounting plate or second shell mounted in the hip bone. In the example shown in FIG. 2, a retaining cap 1 couples ligament 214 in shell 219. Projections 243 are spades capable of fixing the shell 219 in a mounting plate (not shown) that is attached to the hip bone of the patient.

Figure 3:
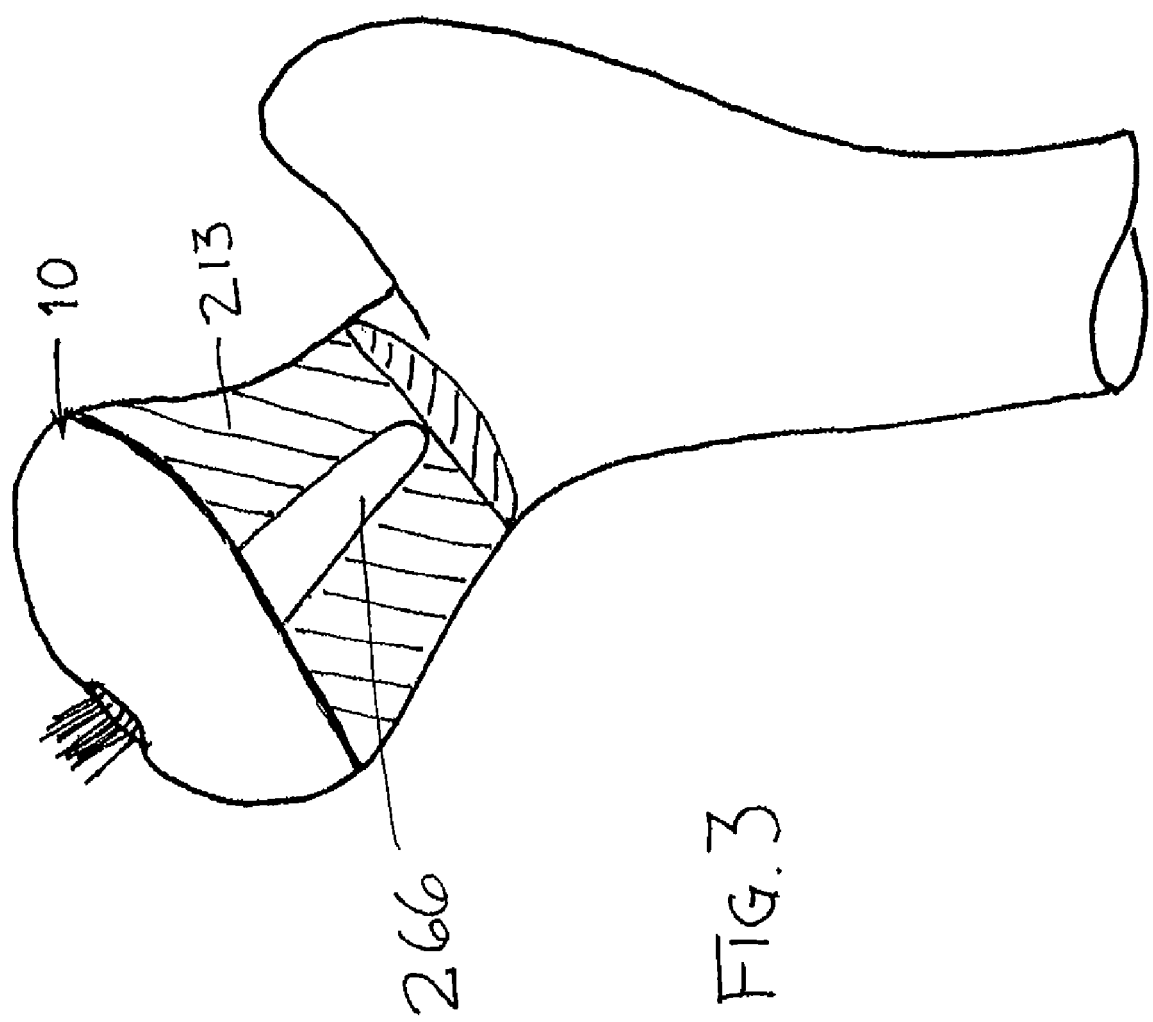
FIG. 3 illustrates a cut-away view of a femur having another example implanted as a cap on a shaved femoral head.

FIG. 3 illustrates a simple attachment mechanism that fits a ball and socket unit 10 (only ball shown) in a femur 213, using only a nail or pin 266 inserted into the femur 213. This procedure greatly reduces the steps necessary for a surgeon to replace a hip joint with a new ball and socket unit 10.

Figure 4A:
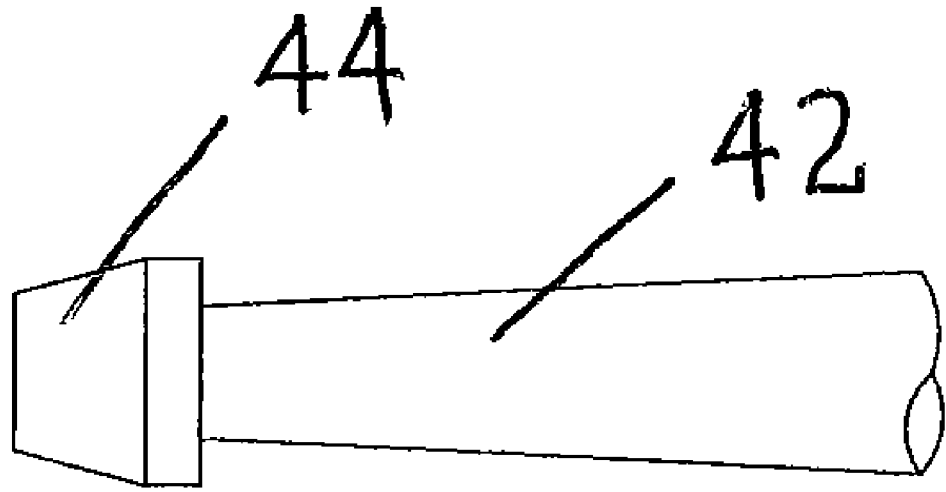
FIGS. 4A and 4B illustrate two embodiments of a neck and connecting end for coupling a conventional femoral implant in a ball of a ball and socket unit.
Figure 4B:
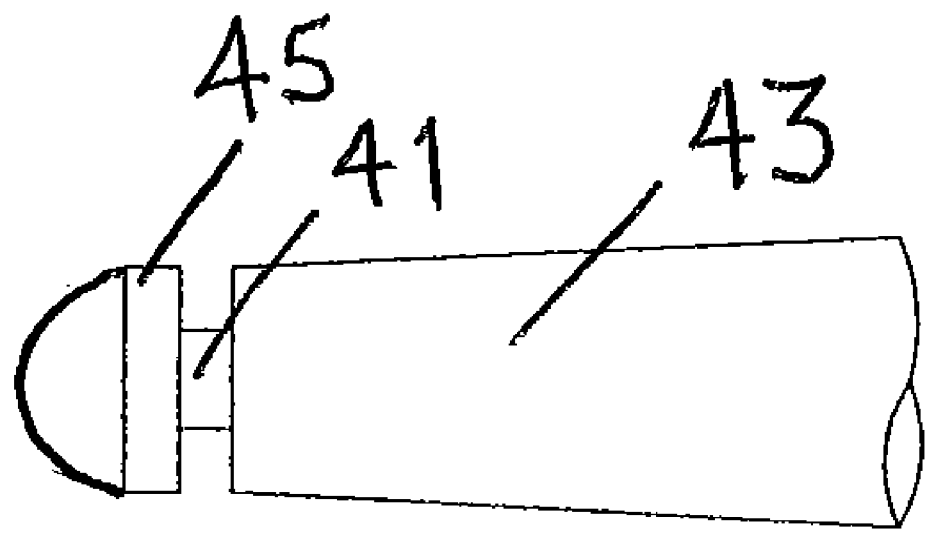
Figure 5:
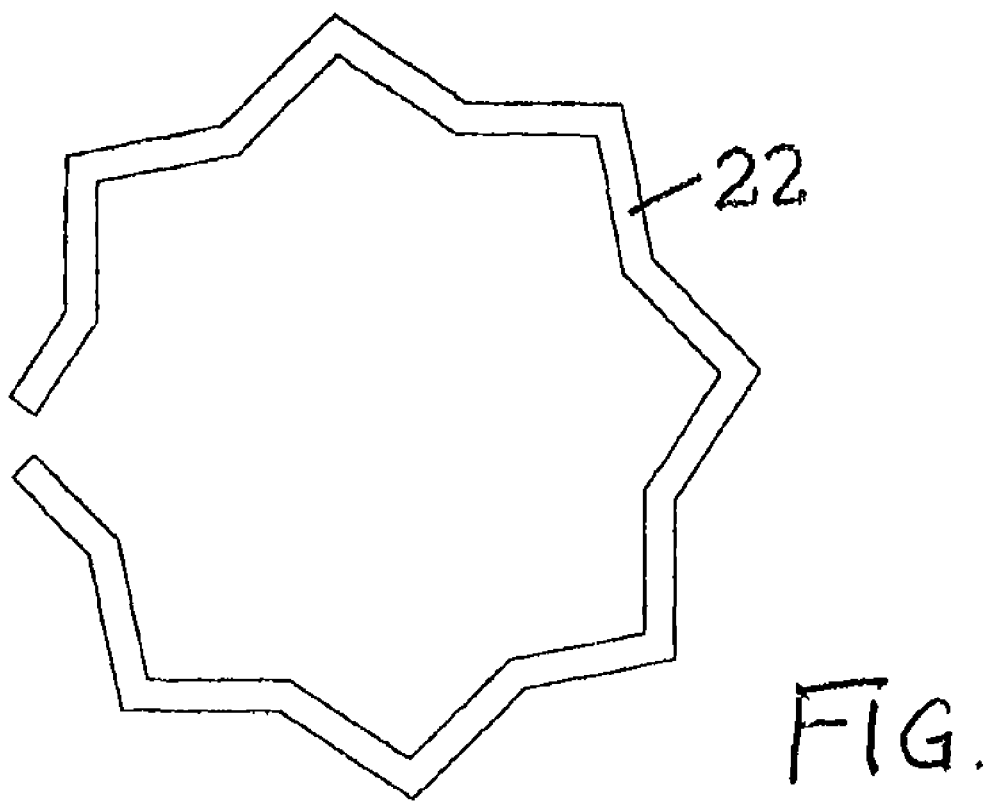
FIG. 5 illustrates a retainer for use with the examples shown in FIGS. 4A, 4B and 6.
Figure 6:
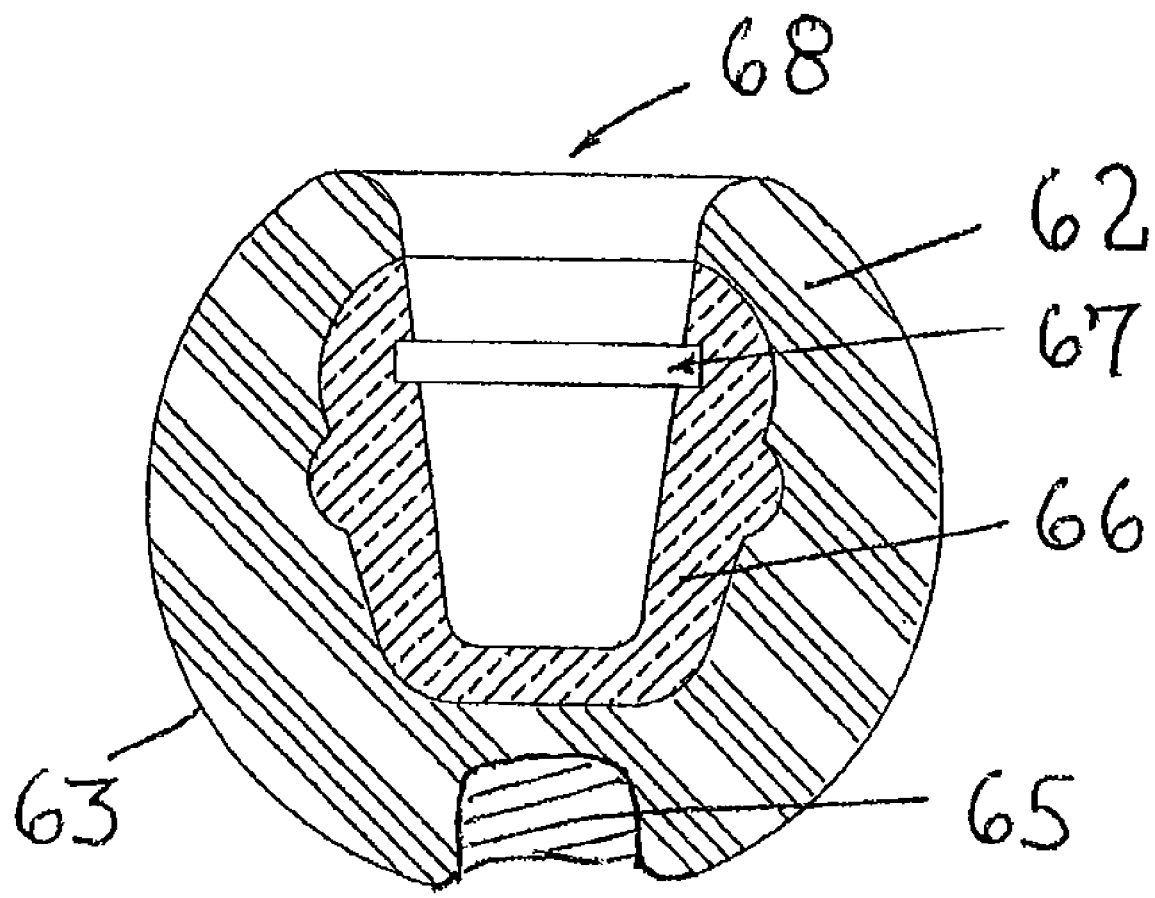
FIG. 6 illustrates a composite ball made of two dissimilar materials for use with in a ball and socket unit.

FIGS. 4A and 4B illustrate two examples of replacement femoral necks 42, 43 coupled to conventional femoral implants (not shown). The free ends 44, 45 are shaped to fit into a cavity formed in a replacement femoral head, such as shown in FIG. 6, for example. The femoral head 62 shown in FIG. 6 is a composite. The wear resistant outer shell 63 may be made of a hard material, such as a ceramic, high density polyethylene with or without cross linking, a metal, or other materials suitably wear resistant and biocompatible for long term use as a prosthesis. The inner liner 66 may be made of a completely different material that reduces stress on the outer shell 63 and provides a toughness suitable for retaining the neck in the ball 62. For example, a neck 42, 43 may be retained in the ball 62 using the retaining ring 22, shown in FIG. 5, for example. Many other fixing mechanisms may be used such as press fit, snap fit, ratchet mechanisms and threading, to name a few. The advantage of the retaining ring is that it is very easy to insert the neck in the cavity 68 of the ball, and a retaining ring may be made removable as known in the art of retaining rings, allowing simple removal of a neck from a ball, if necessary.

Figure 7:
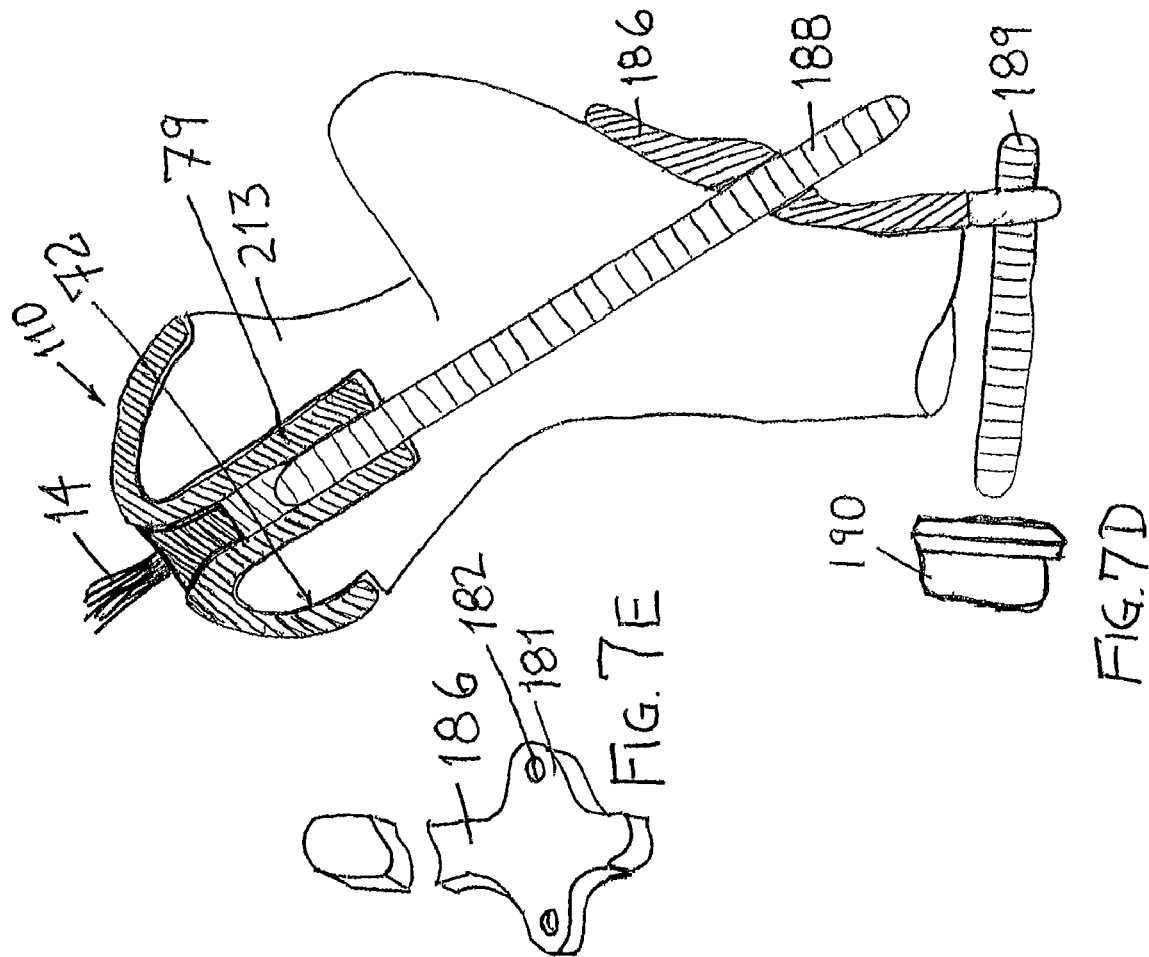
FIGS. 7A-7F illustrate fastening mechanisms for a prosthesis including a ball and socket unit.

In FIGS. 7A-7F, an example of a very flexible fixation system is shown for one example of a replacement ball and socket unit. The socket is not shown, but the socket may be attached to the ball 110 using the ligament 14 to prevent dislocation of the ball from the socket. A guide hole may be bored through the femur 213, as shown in FIG. 7A, for example. The patient's femoral head is shaved using a cutting instrument, a grinder or a laser, for example. A hole is bored in the femoral head of the femur 213 (sizes are not to scale) to accommodate the stem 79 of the ball 110, and the ball and socket unit is positioned on the femur 213. A connector 188 is inserted in the stem 79, which has a one-way ratchet mechanism like a cable tie, such as described in U.S. Pat. No. 5,250,049, for example. Alternatively, the stem 79 may have threads or another coupling mechanism.

In the example shown, the inner surface 72 of the ball 110 is treated to stimulate bone growth and attachment between the inner surface 72 and the new bone. The connector 188 may have its surface treated to stimulate bone growth. In one example, the connector 188 is made of a material that is absorbable by the body of the patient over time, which allows bone to gradually replace the connector 188, which is under a preset amount of tension, when properly fixed by the retention mechanism 186. Resorbable polymers and co-polymers are known from the literature, such as polylactic acid, polyglycolic acid, polydioxanone, polycaprolactone. Osteogenic inorganic additives are known, such as hydroxyapatite and calcium phosphate for controlled growth into the polymeric materials being absorbed. Antibiotics and bone growth stimulants may be included, which may be released over time during absorption, such as etidronate.

The retention mechanism 186 may use a ratchet mechanism, also, which greatly reduces the time required for the surgery. Alternatively, a cap or plug may be threaded onto the end of the connector 188 and may be tightened to a torque that lightly compresses the ball 110 onto the shaved femoral head of the femur 213. Such compression is capable of reducing the time to repair a fracture and is expected to increase the rate of bone growth into a coating. Additional connectors may be used to distribute the load on the retention mechanism 186 to a larger area of the femur 213. Conventionally, lag screws are inserted into the femur 213 through the retention mechanism 186, as is known in the art.

Alternative connectors are shown in FIGS. 7B-7F that provide advantages over conventional lag screws. One advantage is that no hole needs to be bored through the femur 213. In one example, the retention mechanism 186 is coupled to the bone by one or more butterfly fittings 181. A connector 189 may be snaked around the bone and through the holes 182 in the butterfly fitting 181. A backing member 190 may be used to avoid the need for snaking the connector 189 around the femur 213. Instead, the backing member 190 is positioned on the opposite side of the femur 213 from the butterfly fitting 181, allowing a straight or nearly straight insertion of the connector 189 on both sides of the femur 213. By applying a preset tension on the connector 189, which may use a ratchet mechanism, the butterfly fitting 181 and backing member 190 apply a light compression on the femur 213. In one example a tool is used to ratchet the end of the connector 189 at the proper preset tension. The tool may use the same mechanism as a rivet gun to apply a force between the butterfly fitting 181 and the end of the connector 189, for example. When the preset tension is attained, the mechanism of the rivet gun merely slips instead of applying additional tension to the connector 189.

In FIG. 7A, the backing member 190 is shown with a sharp edge 191, which may be inserted into an incision. A flexible or formable material may be bent into a shape, such as shown in FIG. 7F, which allows the backing member 190 to be directed around the bone and into a position on the opposite side of the bone from the retention mechanism 186. For example, a shape change material with a transition temperature less than the body temperature may be use, which changes shape as it warms to the temperature of the patient's body. Thus, the backing member 190 of FIG. 7F may change its shape to that in FIG. 7B, as the shape change material warms to a temperature greater than its phase transition temperature. Materials are known that are capable of a one-way and two-way shape change transition. As bone growth makes the fixation unnecessary, the materials of the backing member 190, connectors, 188, 189, and/or retention mechanism 186 may be absorbed by the body, which has the advantage of avoiding bone density loss, infection and other complications of a rigid fixation mechanism that remains permanently in the body of the patient.

Preferably, the materials used for the prosthesis are selected for wear resistance, bio-compatibility and durability for use as a prosthesis in a patient. Any of the known materials may be used, such as metal on metal articulations, metal on conventional polyethylene articulations, metal on cross-linked polyethylene articulations, cross-linked polyethylene on metal articulations and other articulations, such as composite articulations. In one embodiment, a conventional shell, except for the ligament 14, has a porous coating on the outer surface, such as the shell used in the Pinnacle™ acetabular cup system.[1] The shell may be made of titanium, a titanium alloy, a cobalt chromium alloy, or a cobalt chromium molybdenum alloy, for example. As shown in FIG. 1D, a retention cup 211 may be fixed in the shell using a pressed fit taper, adhesive bonding, pins, extensions, surface tension forces, tabs or tendrils 201 integrally formed and adhered with the ligament 214 in the shell 219 and any other fixation mechanism. The retention cup 211 may have a through passage for the ligament 14, which may be coupled to the shell 219, for example. Alternatively, a cup may be omitted and the shell 219 may serve as the cup, as depicted in FIG. 2.

[1] Pinnacle™ is a trademark of Depuy Orthopedics, Inc.

Figure 8:
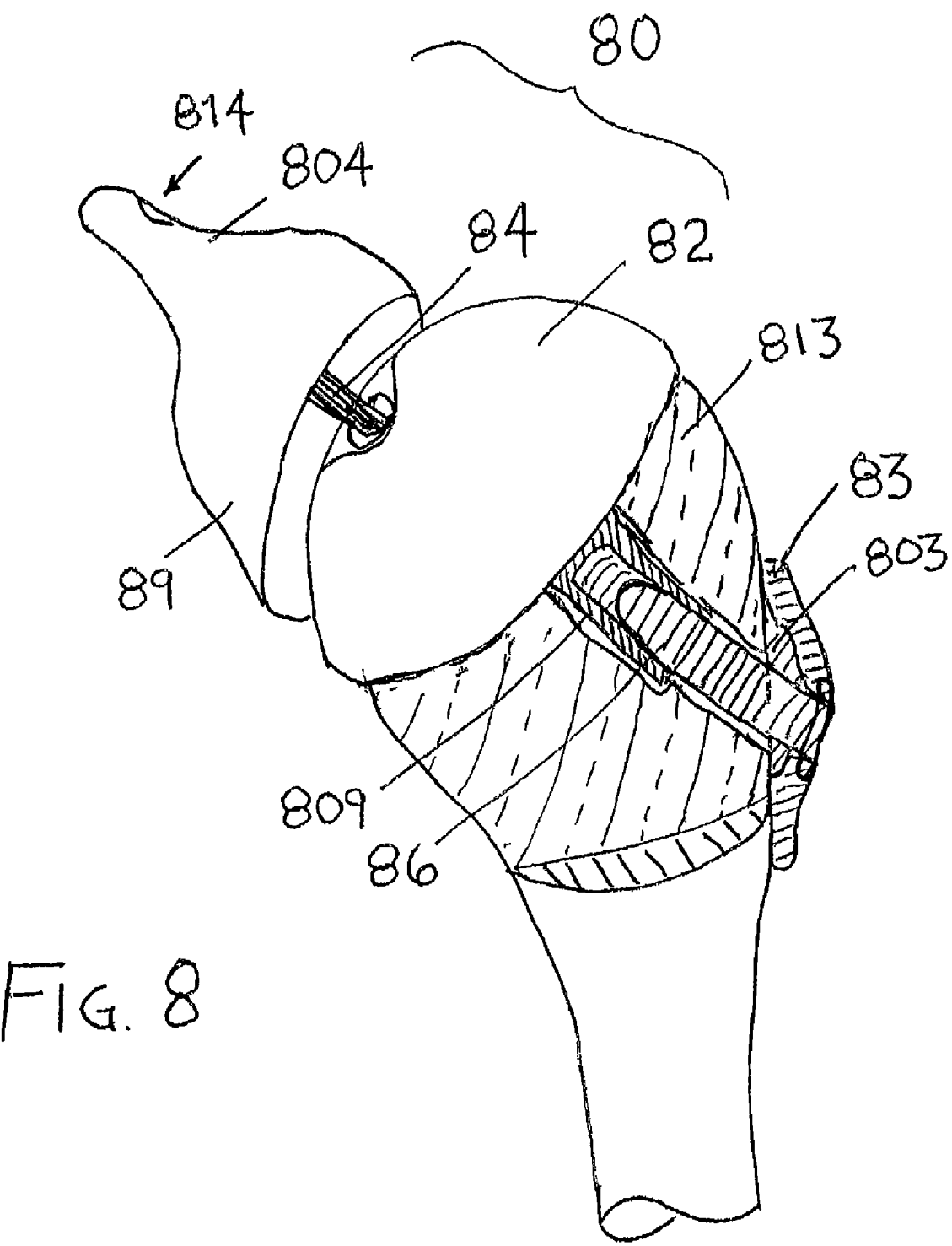
FIG. 8 illustrates a ball and socket unit installed on a humerus bone.
Figure 9:
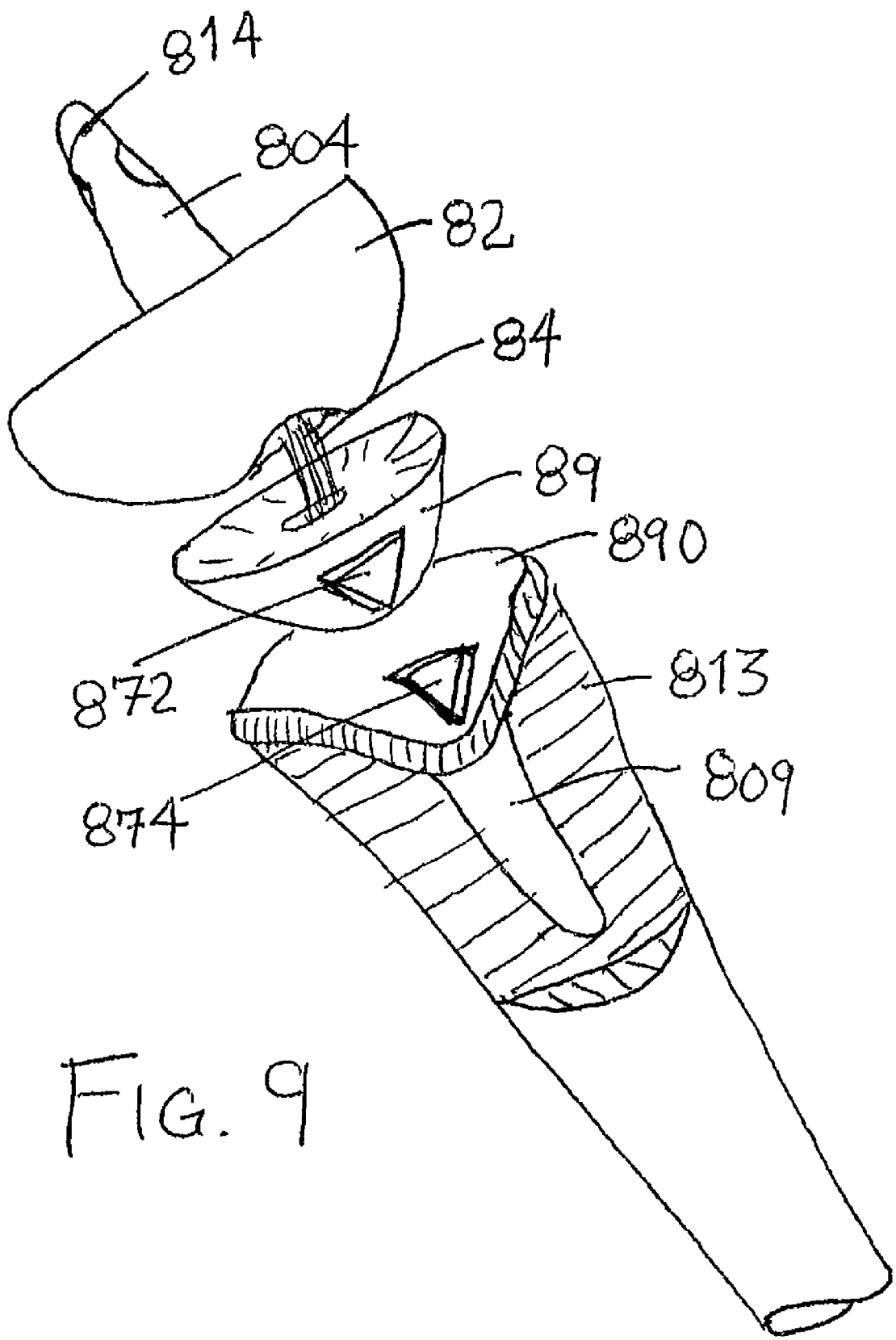
FIG. 9 illustrates another fixating device for reverse mounting of a ball and socket unit on a humerus bone.
Figure 10F:
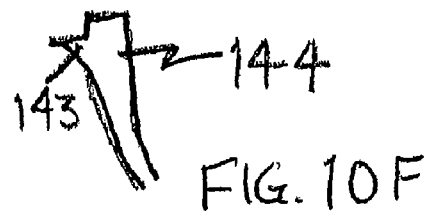
FIGS. 10A-10F illustrate, schematically, some examples of sockets for mounting of a ball and shell unit in the acetabulum.
Figure 10A:
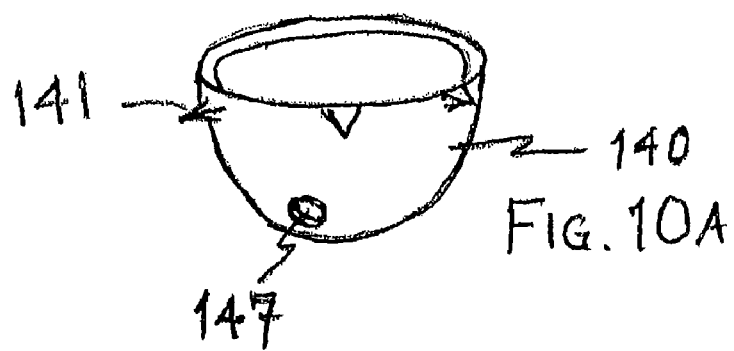
Figure 10B:
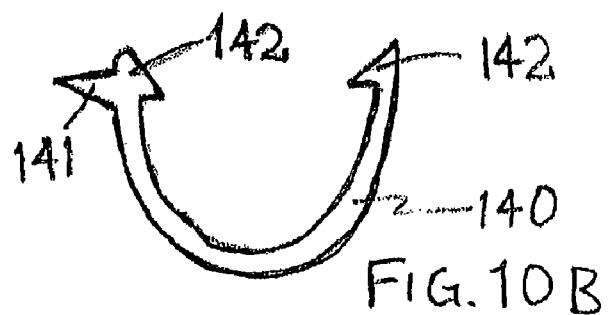
Figure 10E:
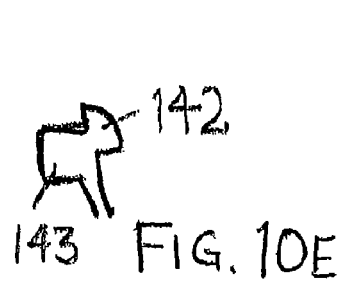
Figure 10D:
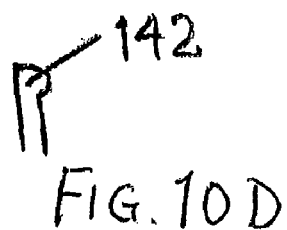
Figure 10C:
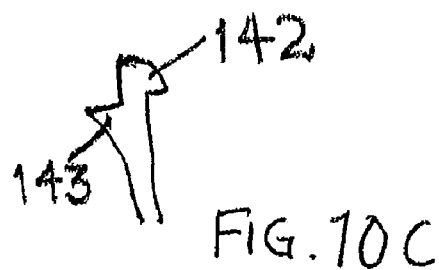

The method of attaching the shell to the hip bone may be the same as used for any conventional shell. Alternatively, the ball and shell unit may be used for any other joint, such as shown in FIG. 8 or a shoulder replacement. The ball and shell assembly 80 is fixed to the bones using a connector 86 to connect the ball 82 and stud 804 with connector hole 814 for shell 89, for example. The process for this embodiment may use the same steps as for a hip replacement, for example. Alternatively, the ball and the shell may be reversed, as illustrated in FIG. 9, fixing the ball to the shoulder and the shell to the humerus.

Figure 13A:
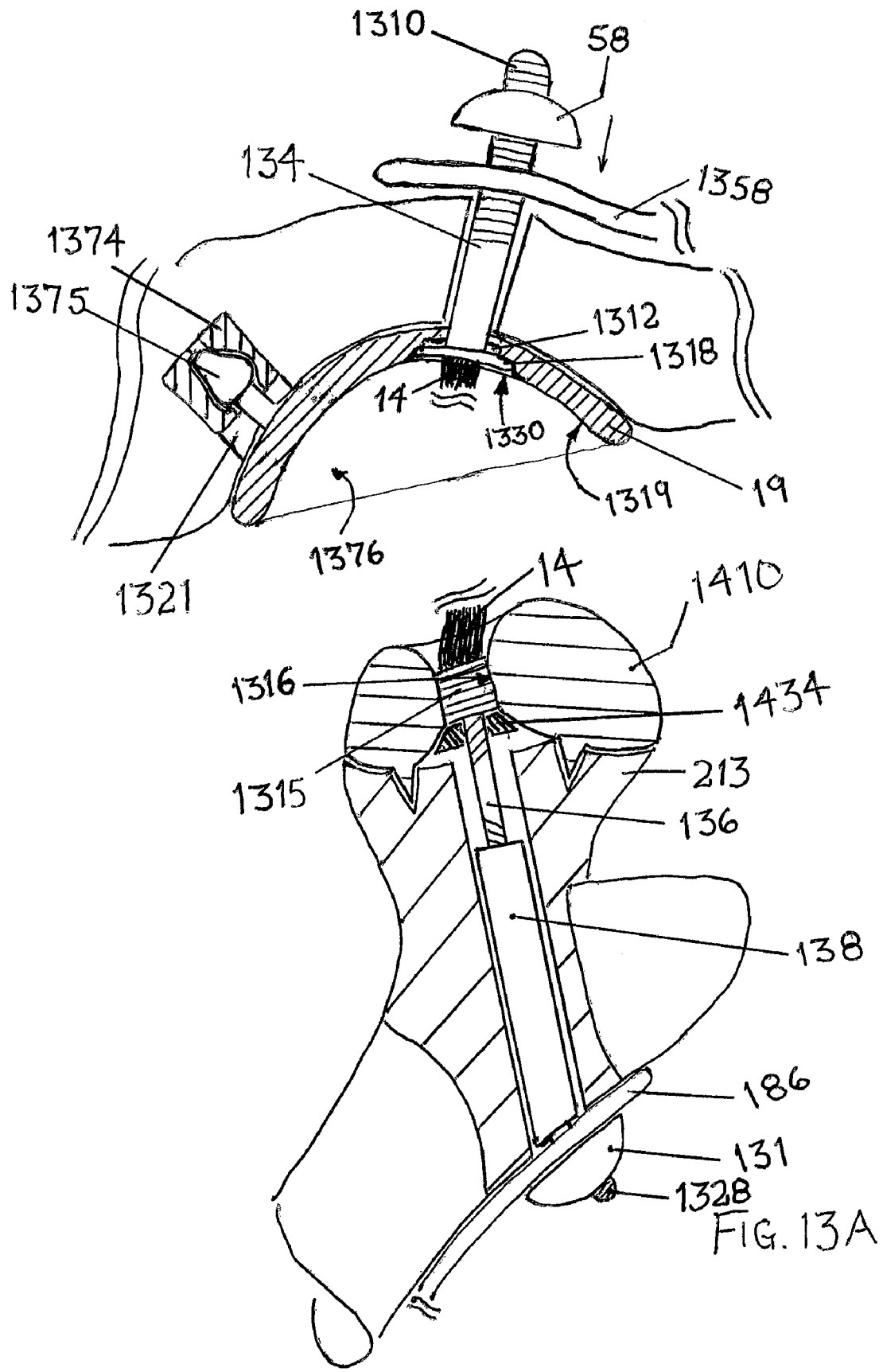
FIG. 13A illustrates another example of a prosthesis for repairing or replacing a joint.
Figure 14:
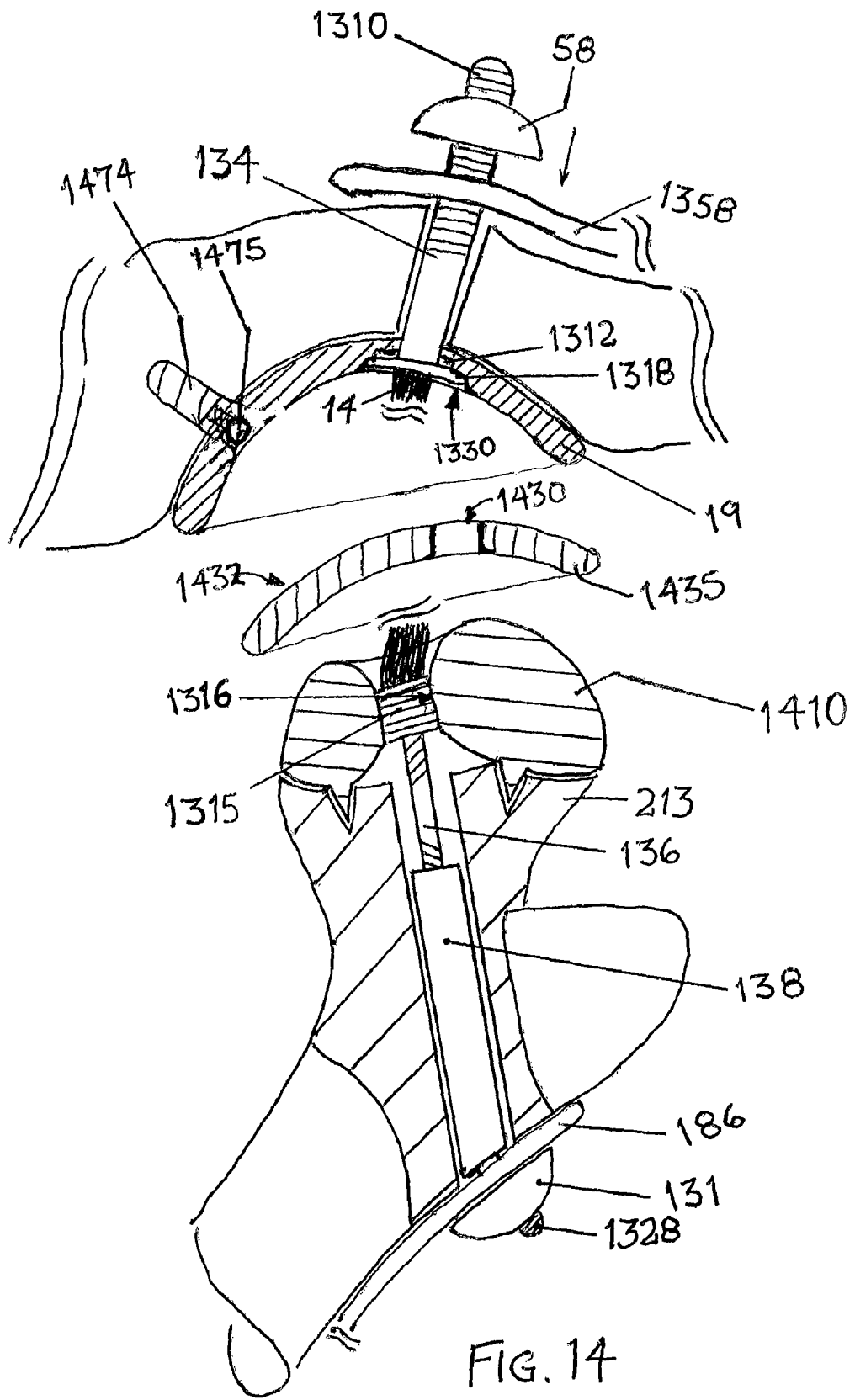
FIG. 14 illustrates an example of a ball and socket unit having a ball and cup unit adhered in a socket and retained by an attachment mechanism through the socket bone.

Inserting the ball and shell as a unit helps to prevent entrainment of debris in the contact area between the ball 82 and the cup 89, reducing undesirable wear associated with debris and reducing the complexity of the surgery. However, a ligament may be used to retain a ball in a cup/shell as shown in FIGS. 13A-14 either as a unit or separately. This has the advantage of permitting screws to be used to fix the shell to the acetabular region of the hip.

For hip and shoulder replacement surgery, a nail or shaft of a prosthesis may be inserted into the long bone of the arm or leg as is known for conventional hip and shoulder replacement surgery. The embodiments shown in some of the drawings may be completed in fewer steps, for example, by eliminating a shaft or nail insertion down the length of the long bone.

Nevertheless, if a gamma nail and neck replacement issued, the ball and socket unit may still be used to make the surgery more efficient. The retention ring 22 in FIG. 5 may be designed to allow a connecting end 44, 45 to be easily inserted into a cavity 68 of a ball 62, such as shown in FIG. 6. The connecting end 44, 45 is then securely retained by the retention ring 22, when the shelf formed between the connecting end 44, 45 and the neck 42, 43 is inserted through the retention ring 22. The shelf prevents the connecting end 44, 45 from being removed from the cavity 68.

The drawings are merely a schematic illustration for use in describing some examples of the present invention and may not be drawn to scale in order to better illustrate the differences in the features depicted. Some of the drawings show exploded views or partial cutaway views for the same reason. Dashed lines in FIG. 2 show a hidden feature.

In one embodiment, a joint prosthesis is used in shoulder joint replacement surgery. In this example, less loads and torque are experienced by the prosthesis, but the range of motion required is extensive. In the example illustrated, the flexibility and percent elastic elongation of the ligament 84 are important design criteria for selection of a material for the ligament 84. Improved flexibility and elongation increases the range of motion of the shoulder. Nevertheless, materials may be used that restrict mobility somewhat without causing dislocation of the shoulder joint. Preferably, a composite material of flexible polyethylene strands combined with a silicone rubber is used to provide superior strength and elasticity. In addition, a natural ligament may be used.

In FIG. 9, another shoulder replacement prosthesis is shown, which illustrates that the ball 82 and shell 89 may be reversed in orientation compared to an anatomical ball and shell for a shoulder joint. In this example, the shell 89 has a v-shaped quick connect attachment 872 that is capable of mating with one of the similarly shaped connections 874 of the mounting plate 890, which is affixed to the humerus 813, for example. The ball 82 is coupled to the bones of the shoulder by a pin 804 and connector (not shown), which may extend through a hole 814, for example.

Similar fixation may be used for finger joints, knees and any joint where pre-formed ligaments in a unit joint that is pre-assembled is suitable. In finger joints, pre-assembly makes rapid surgical procedures possible. In knee joints, ligaments provide excellent stability comparable to anatomical knee joints.

In one example, such as shown in FIGS. 10A-10F, a material is used to provide a soft socket 140. The soft socket 140 is made of a deformable material having the capability of transferring a load to surrounding bone. The deformable material may be polymer, a metal or a combination of these, for example. If a metal, the thickness and alloy is selected to provide super elastic properties, for example. If a polymer, the material is selected to provide elasticity of the shell and sufficient rigidity of the retention mechanisms, such as shown in FIGS. 10B-10F, to retain a ball and shell unit within the socket. High density polyethylene may be used, for example.

A soft socket may be attached to the bone using screws inserted through screw holes 147 in the soft shell 140. Alternatively or in addition to screws, rigid prongs 141 may extend through, or extend from the outer surface, of the soft shell 140. In one example, a ridge 143 extends from the outer surface of the soft shell 140, which may be shaped to fit into a contour cut into the bone of the patient, such as the pelvic bone. In this case, a ridge 143 may be made of the same material as the soft shell 140. The soft shell 140 may be deformed to insert it into a cavity formed using a blade, reamer or other tool that is capable of shaping a cavity in the bone for receiving the socket. A channel formed by the tool may be shaped to receive the ridge 143. By inserting a rigid cup and ball, as previously presented herein, the soft shell 140 may be locked in the cavity formed in the bone of the patient. An extension 142 on the inner surface is capable of retaining a cup, or the inner surface of the shell may be formed for a pressure fitting 144.

In yet another embodiment of a socket 150, the socket 150 comprises a plurality of leafs 158 that are capable of flexibly bending inward and outward. Each of the leafs 158, which are capable of flexibly bending inward and outward, are made of a material that is flexible, based on the thickness and width of the leaf 158. Each leaf 158 may have a pressure fitting (not shown) or an extension 152 capable of latching a ball and shell unit, previously described, within the socket 150 when the socket 150 is mounted in a cavity formed in the bone of the patient.

In one example, the socket 150 is formed of a shape change material, such as an alloy of nickel and titanium that is capable of undergoing a phase transition at a phase transition temperature or any other phase change alloy. In this case, the leafs 158 may be deformed to allow the diameter of the shell to be greatly reduced. If the phase change temperature is less than the temperature of a body of a patient, the socket may be inserted through a comparatively small diameter hole at a temperature below the phase change temperature. Upon inserting the socket 150 in this initial deformed shape into the cavity formed in the bone, the socket 150 will become warmer. When the phase change temperature is reached, then the leafs 158 of the socket 150 will extend outward latching the socket 150 into the cavity formed in the bone.

In one example, the socket 150 is made of a two-way shape change material, such that the socket may be removed from the body of the patient merely by cooling the leafs 158 of the socket 150 to below the phase change temperature, which will cause the leafs 158 to move inwardly into the deformed configuration, allowing the socket to be removed and repositioned or replaced, for example.

Figure 11D:
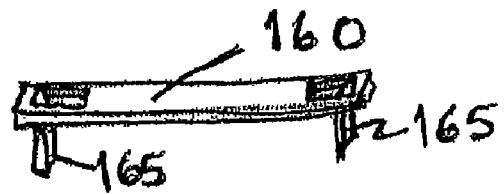
FIGS. 11A-11D illustrate, schematically, an additional example of a socket for mounting of a ball and shell unit in an acetabulum.
Figure 11A:
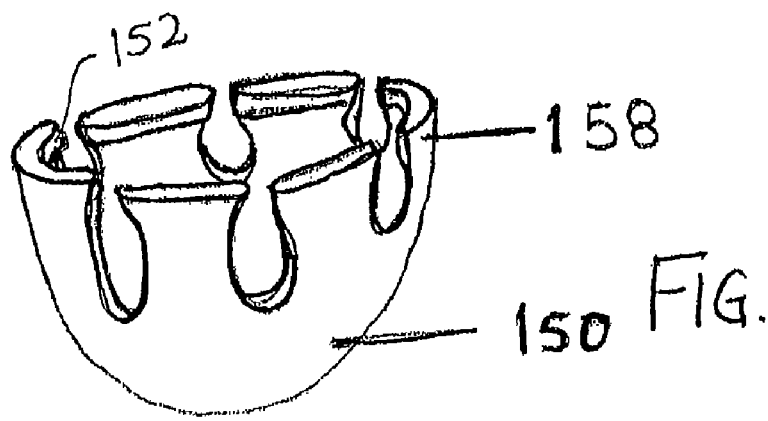
Figure 11C:
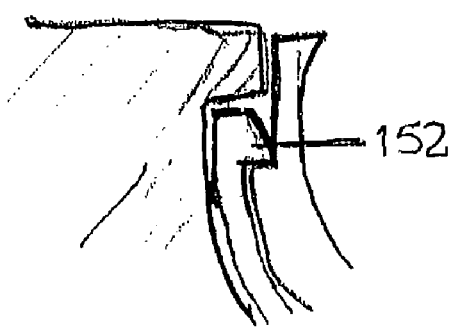
Figure 11B:
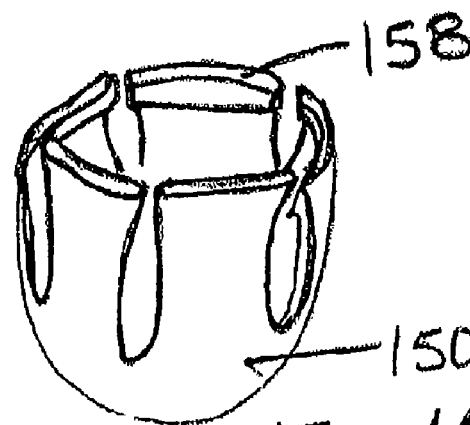
Figure 12:
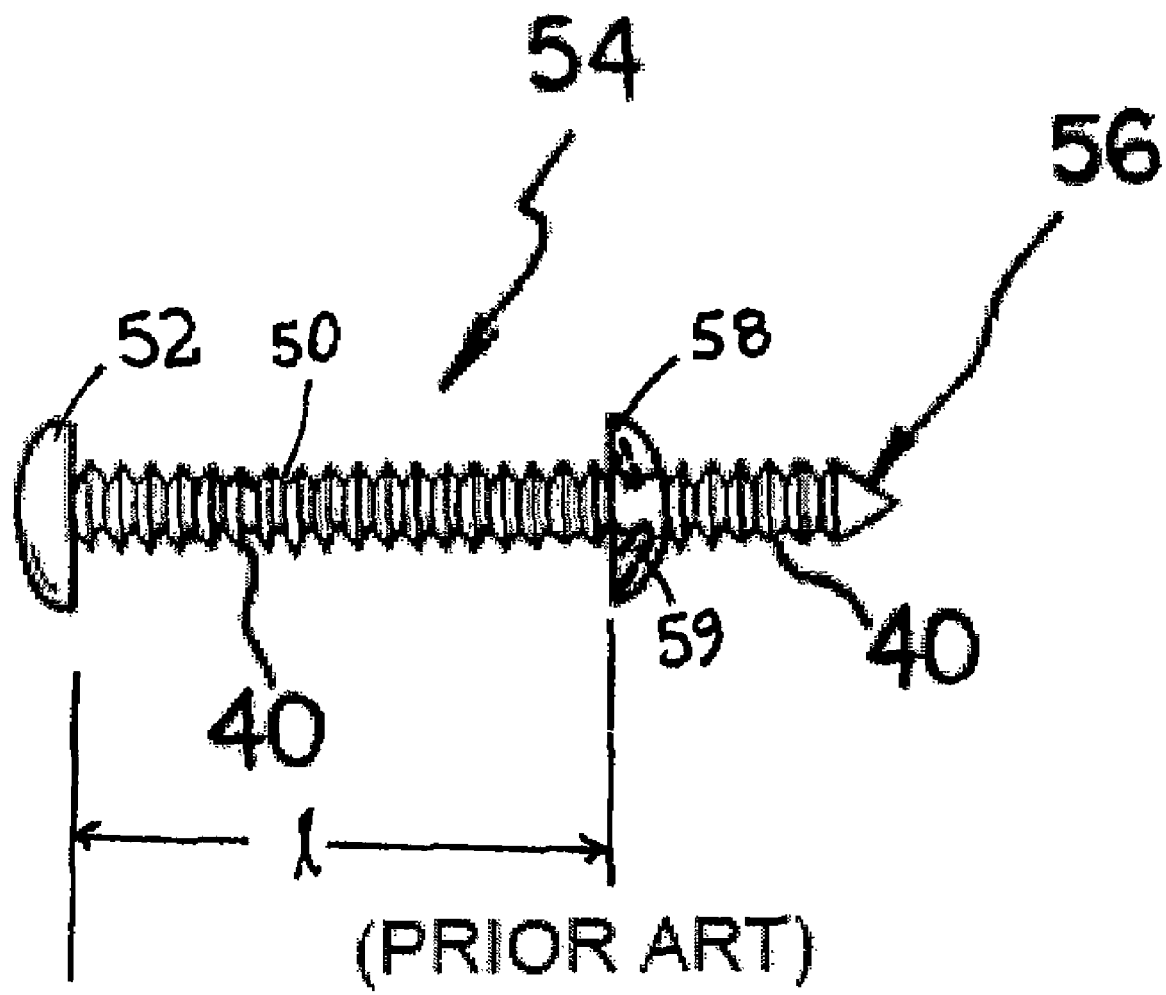
FIG. 12 shows a prior art fixation device.

In other examples, the socket 150 is made of an elastic material, allowing the leafs 158 to be deformed elastically, but with the capability of springing back into the undeformed configuration when fit into the cavity formed in the patient's body. In this case, the cup and ball assembly, described previously, positively fixes the socket 150 into the cavity. Additionally, the ball and shell unit may have fixation devices 160, such as illustrated in FIG. 11D, with spikes 165 that extend into the surrounding bone through gaps between the leafs 158. For example, a fixation device 160 may have two spikes 165 attached by a spring member 160 that may be inserted between a socket 150 and a cup and ball assembly. For example, a channel may be formed in either or both of the cup and/or the shell to accommodate the thickness of the spring member 160. The spring member 160 may serve an additional function by applying a positive bias between the ball and shell unit and a retaining member 152 of the socket 150.

In another example, the shell and ball unit may have interlocking teeth at the end and can include holes to allow bone growth or addition of a porous material.

In FIG. 13A, an attachment mechanism 134 is shown to include a fixation device having a ratchet connector 58 with ratchet mechanism 59 for engaging ridges on a first coupling member 1310. A plate 1358 may be used to spread stresses over a large area of the pelvis or to reconstruct or strengthen a weak or damaged pelvic bone. The attachment mechanism attaches to a first bone. The attachment mechanism also includes a ligament 14 and a second coupling member 1315. The attachment mechanism passes through a shell 19 and couples the shell 19 to the pelvic bone using the retainer 1330, which may include a key 1312 to prevent rotation of the first coupling member 1310 using a locking channel 1334 as shown in FIG. 13D. A countersink 1332 allows the retainer 1318 to be recessed below the inner surface 1319 of the shell 19.

In this example, a bushing 1374 is shown engaging a compression member 1375 extending from the convex surface of the shell 19. The bushing 1374 may be any biocompatible elastic material, such as silicone, capable of being compressed into the bone surrounding a hole formed in the pelvis. The bushing may be inserted as a visco-plastic material that sets up over time or may be a sponge of a material suitable for bone ingrowth such materials are well known in the art. In FIG. 14, the compression member 1475 is removably attached to the shell 19, and a liner 1432 comprises a body 1435 having a hole 1430 through the body. The compression member 1475 engages the bushing 1474 with the shell 19.

An extension member 136 is capable of threadingly coupling with internal threads 1353 of the second coupling member 1315. A cannulated member 138 is threadingly attached to the opposite end of the extension member. The cannulated member may have ridges along an exterior surface or may be threaded to an intermediate member 1326, such as shown in FIGS. 13A and 13F, in greater detail.

In addition, a retention mechanism 186 is shown disposed on at a bottom surface of a bone, which provides additional support for a cap 131 tensioned on the cannulated member 138. At a capped end 131, and end 1327 of a retainer 1326 is shown extending outward. this end 1326 may be easily cut flush with the surface of the cap 131. The second coupling member 1315 may be fixed in the ball 1410 by press fit, bonding, threading or any other mechanism provided that it locks into the cavity without loosening.

In FIGS. 13B-C, an attachment mechanism includes a fixing device 1350 having a ratchet mechanism 59, a first coupling member 1310, a ligament 1314, and a second coupling member 1315. The ligament couples the first coupling member 1310 to the second coupling member 1315, and the first coupling member 1310 has external ridges capable of engaging the ratchet mechanism 59 of the cap 58. The other end of the first coupling member 1310 has a flange 1318 shaped to mate with a countersunk portion 1332 of the shell 19 and a key portion 1312 extending from a surface of the flange 1318. The key portion 1312 being capable of interlocking with the locking channel 1334 of the shell 19.

In FIG. 13D, a cross section of a shell 19 is shown having an arcuate inner surface 1319 and a hole 1330 passing through the shell 19 and the arcuate inner surface 1319. A locking channel 1334 extends into the hole 1330 in the shell 19, and a countersunk portion 1332 surrounds the hole, extending into the arcuate inner surface 1319.

In FIG. 13E, the second coupling member 1315 of the attachment mechanism has a threaded exterior surface 1352 capable of coupling with a threaded inner surface of a ball unit and includes a cavity 1360 having internal threads 1353. Slots 1357 may be used for threadingly inserting the coupling member 1315 into the cavity formed in the head of the ball unit 1410. In on example, the attachment mechanism 134 is fixed in the ball and shell by inserting the first coupling end 1310 through the hole defined by the threaded surface 1316 in the ball 1410 and then through the hole 1330 in the shell. The flange 1318 in this example is smaller than the diameter of the threaded surface 1316 of the ball 1410. Alternatively, the coupling member 1315 in the ball may be formed in place using an epoxy resin, for example. Then, a barrier 1434 is used to hold the extension 136 or other coupling member in place as epoxy is injected to form a plug in a cavity formed in the ball 1410, for example. In FIG. 13F, an intermediate retainer 1326 is shown including a first portion 1327 and a second portion 1328, with each extending an elbow of the retainer 1326.

Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. A prosthesis for repairing a joint between a bone having a ball portion of the joint and a socket structure in a patient, comprising:
    a shell having an arcuate inner surface and a hole passing through the shell and the hole has a countersunk portion extending from the inner surface;
    a ball unit having an arcuate outer surface capable of articulated motion in the arcuate inner surface of the shell and a cavity extending into the ball unit from the arcuate outer surface of the ball unit;
    a first fixing device and a second fixing device, each having a ratchet mechanism;
    an attachment mechanism comprised of the first fixing device, a first coupling member, a ligament, and a second coupling member, wherein the ligament couples the first coupling member to the second coupling member, and the first coupling member has a first end and a second end opposite of the first end, the first end having external ridges capable of engaging the ratchet mechanism of the first fixing device, the second end having a flange shaped to engage with the countersunk portion of the shell and the second coupling member is capable of coupling with the cavity of the ball unit;
    an extension member capable of coupling to the second coupling member; and
    a coupling device comprising a cannulated member and the second fixing device, the cannulated member having a first end and a second end, opposite of the first end, and ridges extending from an exterior surface of the cannulated member, the second fixing device having a contact surface, such that, when the prosthesis is surgically implanted in the patient, the ball unit is capable of being attached to the bone having the ball portion, after removing a portion of the ball portion, and the contact surface of the second fixing member is capable of operably contacting a surface of the bone opposite of the ball unit, tensioning the cannulated member between the first end of the cannulated member attached to the extension member and the second end of the cannulated member capable of being attached by the ratchet mechanism of the second fixing device to the surface of the bone opposite of the ball unit.

2. A ball and socket unit for a prosthetic ball and socket joint used in repair of a joint in a patient, comprising:
    a shell having an arcuate inner surface, a hole passing through the shell and the arcuate inner surface, and a countersunk portion surrounding the hole in the arcuate inner surface;
    a ball unit, having an arcuate outer surface capable of articulated motion in the arcuate inner surface of the shell; and
    an attachment mechanism comprised of:
    a fixing device having a ratchet mechanism,
    a first coupling member,
    a ligament,
    and a second coupling member,
    wherein the ligament couples the first coupling member to the second coupling member, and
    the first coupling member has a first end and a second end opposite of the first end, the first end having external ridges capable of engaging the ratchet mechanism of the fixing device, the second end having a cylindrical surface and a retainer extending outwardly from the cylindrical surface, and the second coupling member being coupled to the ball unit of the ball and socket unit such that the retainer of the second end of the first coupling member fits in the countersunk portion of the hole of the shell retaining the second end of the first coupling member in the hole of the shell.

3. The prosthesis according to claim 2, further comprising:
an extension member coupling the ball unit to a coupling device capable of fixing the ball unit to a bone of the patient.

4. The prosthesis according to claim 3, wherein the shell is capable of being fixed to a socket structure of the patient using a bushing member capable of being implanted within a hole formed in the socket structure of the patient and a compression member attached to the shell and inserted into the bushing member outwardly compressing the bushing member into the sides of the socket structure defining the hole formed in the socket structure.

5. The prosthesis according to claim 4, wherein the compression member is removably attached to the shell.

* * * * *